Figure 1:
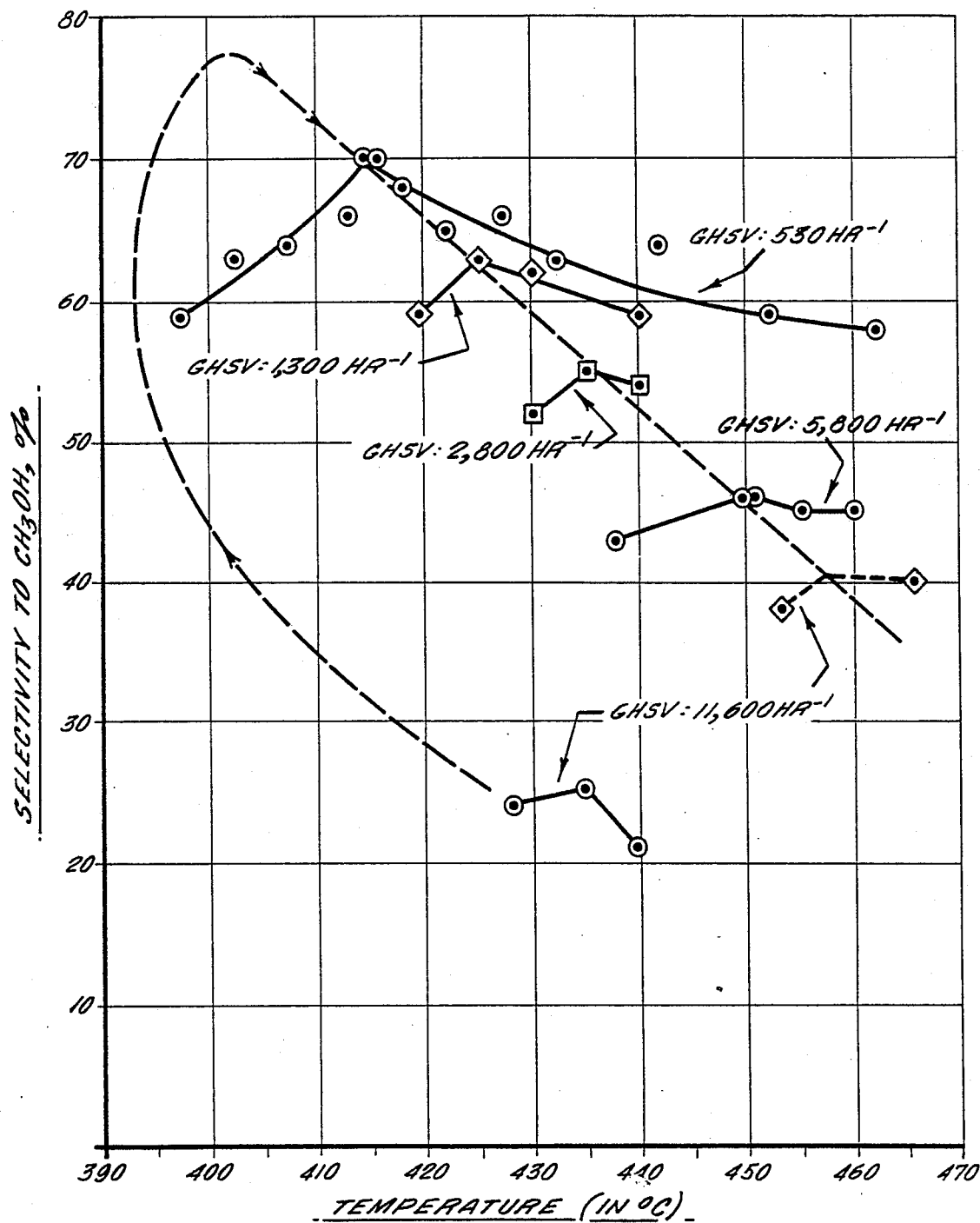

United States Patent [19]

Durante et al.

[11] Patent Number: 4,918,249
[45] Date of Patent: Apr. 17, 1990

[54] SILICOMETALLATE MOLECULAR SIEVES AND THEIR USE AS CATALYSTS IN OXIDATION OF ALKANES

[75] Inventors: Vincent A. Durante, West Chester; Darrell W. Walker, Media; Steven M. Gussow; James E. Lyons, both of Wallingford, all of Pa.

[73] Assignee: Sun Refining and Marketing Company, Philadelphia, Pa.

[21] Appl. No.: 338,916

[22] Filed: Apr. 17, 1989

[51] Int. Cl.⁴ .............. C07C 29/50; C07C 31/04; C07C 2/00
[52] U.S. Cl. ................... 568/910; 568/399; 568/475; 568/910.5; 585/700
[58] Field of Search .............. 568/910, 910.5, 399, 568/375; 585/700

[56] References Cited

U.S. PATENT DOCUMENTS

| 4,165,340 | 8/1979 | Tohzuka et al. | 568/399 |
| 4,472,314 | 9/1984 | Conner et al. | 568/475 |
| 4,605,805 | 8/1986 | Chang et al. | 585/700 |
| 4,607,130 | 8/1986 | Chang et al. | 585/700 |
| 4,707,500 | 11/1987 | Hinnenkamp et al. | 585/700 |
| 4,803,187 | 2/1989 | Lyons et al. | 568/399 |

FOREIGN PATENT DOCUMENTS

| 30088 | 6/1981 | European Pat. Off. | 568/399 |
| 2743113 | 3/1979 | Fed. Rep. of Germany | 568/910 |
| 3406751 | 8/1985 | Fed. Rep. of Germany | 585/700 |

Primary Examiner—J. E. Evans
Attorney, Agent, or Firm—J. Edward Hess; Donald R. Johnson

[57] ABSTRACT

Silicometallates containing iron in the structural framework are employed as catalysts for the oxidation of hydrocarbons or oxygenated hydrocarbons, for example the vapor phase oxidation of methane to methanol.

13 Claims, 2 Drawing Sheets

SILICOMETALLATE MOLECULAR SIEVES AND THEIR USE AS CATALYSTS IN OXIDATION OF ALKANES

This invention relates to zeolitic materials in which some framework silicon atoms are substituted with iron, and the use of such materials in the oxidation of alkanes, for example the vapor phase oxidation of methane to methanol. Materials according to the invention have been found to catalyze such oxidation in a single step with acceptable yield and selectivity.

The conventional method for conversion of methane to methanol involves a first reaction with water to produce synthesis gas, a mixture of carbon monoxide and hydrogen, followed by catalytic conversion of the synthesis gas to methanol. A direct oxidation of methane to methanol would be simpler and preferable.

United Kingdom Pat. No. 1,244,001 discloses oxidation of methane to methanol over a catalyst consisting of $(Mo_2O_3)\cdot Fe_2O_3$ on silica/alumina (25% $Al_2O_3$/75% $SiO_2$) sintered to 0.1 g/cm$^2$ at 1000° C.) in 65% selectivity (moles methanol/moles Product $\times$100) at 2.1% conversion. The temperature is 439° C. and the pressure 52 atmospheres. Temperatures, pressures and space rates in the process disclosed in this patent are 300°-550° C.; 5-150 atmospheres and 20,000-50,000 hr$^{-1}$, respectively.

Gesser et al U.S. Pat. No. 4,618,732 discloses oxidation of methane-containing natural gas of undefined composition to methanol in a glass-lined reactor with no catalyst packing to obtain selectivities as high as 92% at 13% conversion (Table 1). The natural gas and oxygen are intimately mixed prior to the reaction. The reaction temperature is generally in the range of 300° to 500° C., and the pressure in the range of 10 to 100 atmospheres, and the residence time of the gases in the reaction zone is normally in the range of 2 to 1000 seconds. The amount of oxygen in the oxygen/methane mixture is preferably in the range of 2 to 20% by volume.

Yarlagadda, Morton, Hunter and Gesser, Ind. Eng. Chem. Res. 1988, 27, 252-256, "Direct Conversion of Methane to Methanol in a Flow Reactor," disclose that methanol selectivities of 75-80% at 8-10% conversion levels per pass could be obtained during the partial oxidation of methane in a glass-lined reactor operated at about 65 atmospheres, 450° C. and gas hourly space velocity of about 400 hr$^{-1}$ (150-750 hr$^{-1}$). Oxygen concentrations less than 5% and reaction pressures higher than 50 atmospheres were found to be conducive to higher methanol selectivity.

According to one embodiment of the present invention, compositions containing silicometallate molecular sieves are used as catalysts to obtain improved results in the oxidation of alkanes such as methane to alcohols. Specifically, the process of this invention achieves selectivities and conversion similar to those reported by Yarlagadda et al. at higher space rates while providing greater conversion then reported in UK Pat. No. 1,244,001 supra. The catalysts according to the invention contain crystalline silicometallates or zeolites with both iron and silicon incorporated in the structural framework. Additional iron which is not part of the zeolitic framework may also be present. Other metals may also be present either in the framework, as exchangeable ions, or as occluded species which are neither exchanged nor part of the framework. These species in addition to iron and silicon may exist as neutral monometallic compounds or as oligomers; they may or may not be crystalline. Examples of elements which may be present as ions, as neutral monomeric compounds, or as oligomers in addition to iron and silicon are Cr, V, Co, Mo, Mn, Ru, Pt, U, Sn, Sb, Bi, Te, Al, B, Ga, Ge, Zr, Ti, P, S. Binders may also be added to the catalyst composition.

An example of a material which may be used as a catalyst in the process according to the invention is the ferrisilicate (silicoferrate) analog of sodalite as disclosed by Szostak and Thomas in Chem. Commun., 1986, page 113, prepared by adding short-polymeric-unit aqueous sodium metasilicate to aqueous iron nitrate, acidifying to form a gel, adding tetramethylammonium chloride to the gel and heating in an autoclave to provide a white powder with an x-ray pattern characteristic of the cubic sodalite structure. Ferrisilicate analogs of ZSM-5 and mordenite have also been disclosed in references cited by Szostak et al supra.

In Szostak, "Molecular Sieves, Principles of Synthesis and Identification," Van Nostrand Reinhold Catalysis Series, Van Nostrand Reinhold, New York 1989, in Table 4.1 on pages 209–210, various metallosilicate molecular sieves containing iron in ZSM-5, levynite, and mordenite structures are disclosed as having been patented; on page 232, referring to work of Iton et al, ferrialuminosilicate analogs of the zeolite ZSM-5 with a reported x-band in the e.s.r. at 4.28, consistent with the presence of some structural iron, is disclosed, the focus of this work being on preparing a shape-selective iron-containing molecular sieve for use as a Fisher-Tropsch catalyst, activity for the latter being related to the presence of non-framework iron; on page 233, referring to work of Calis et al, preparation of ferrisilicate molecular sieves using a published method for preparing zeolite ZSM-5, except for replacing the aluminum source with ferric nitrate, is disclosed; on page 237, it is disclosed that iron is thermally less stable in the silicate framework than aluminum; on page 238, it is disclosed that the Mossbauer spectrum of ferrisilicate with the ZSM-5 structure and $SiO_2/Fe_2O_3$ of 98 indicate extremely high dispersions of octahedral iron oxide in the material, this highly dispensed nonframework iron having been found to contribute significantly to the catalytic activity of the bulk material.

Silicometallate molecular sieves have been disclosed for use as catalysts for various reactions as noted subsequently.

In U.S. Pat. No. 4,208,203 crystalline ferrosilicate molecular sieves useful inter alia as catalysts for aromatisation of Fischer-Tropsch synthesis products, aromatisation of methanol and/or of dimethyl ether and production of aromatic hydrocarbons from $H_2/CO$ mixtures are disclosed.

In U.S. Pat. No. 4,708,857, synthetic crystalline iron-borosilicates useful as catalysts for converting methanol and/or ethanol or synthesis gas to high octane gasoline are disclosed.

In European Pat. No. 115031-A, Aug. 8, 1984, microporous crystalline ferrisilicate molecular sieve useful as adsorbent, catalyst for example hydrocarbon conversion catalyst and ion exchanger, is disclosed.

In European Pat. No. 108271, May 16, 1984, ferrosilicate molecular sieve useful as adsorbent and catalyst for example hydrocarbon cracking catalyst and useful as catalyst or catalyst support in processes wherein zeolites and especially mordenite are effective, is disclosed.

In European Pat. No. 72054-A, Feb. 16, 1983, the preparation of metal, preferably aluminum or iron, silicates useful inter alia as catalyst for conversion of dimethyl ether, methanol or other lower alcohols to hydrocarbons including olefins and aromatics, and various hydrocarbon reactions, is disclosed.

In European Pat. No. 64328-A Nov. 10, 1982, metal, including iron, containing high siliceous beta zeolites useful as catalysts for hydrogenation, dehydrogenation, desulphurization, olefin polymerization and the conversion of alcohols to hydrocarbons etc., are disclosed.

In European Pat. No. 10572-A, May 14, 1980, synthetic crystalline iron silicate having a zeolite structure useful in cracking and hydrocracking processes and in the conversion of methanol to unsaturated hydrocarbon is disclosed.

In Japanese Pat. No. J58110421-A, July 1, 1983, crystalline iron aluminosilicate useful as catalysts for production of hydrocarbon especially ethylene and propylene is disclosed.

In Japanese Pat. No. J57011818, Jan. 21, 1982, crystalline trivalent transition metal organosilicate-containing organic sulphur compound useful in the production of aromatic hydrocarbon mixture from methanol or in the conversion of various organic compounds is disclosed.

In Japanese Pat. No. J57007820, Jan. 16, 1982, crystalline trivalent transition-metal organosilicate useful as catalysts in a conversion reaction and carrier for catalyst is disclosed.

According to one embodiment of the present invention, silicometallates containing iron in at least a portion of the structural framework are employed as catalysts. Aluminum, gallium, germanium, boron, phosphorus, vanadium and the like may optionally also be present as framework elements of the crystalline structures so long as iron and silicon are also present. If the predominant tetrahedral atom is silicon and the non-silicon framework-metal ions or complexes are of formal charge or valence other than $+4$, then ion exchange capacity may develop in the structure. Exchange ions may then also be present. If the frameworks are negatively charged due to isomorphous substitution for silicon of iron or other elements or oxocomplexes of these elements of formal charges less than $+4$, these exchange ions can be any suitable cations including but not limited to $H+$, $Na+$, $K+$, $NH_4+$, $NR_4+$ where R is a hydrocarbon radical, $Ca^{2+}$, $Fe^{3+}$, $Fe^{2+}$ and the like or cationic coordination complexes of metals. If the frameworks are positively charged due to substitution of silicon by an iron-containing entity of formal charge greater than $+4$, then the frameworks may develop anion exchange capacities. Inorganic or organic anionic species can then be incorporated into the active compositions by ion exchange. If the nonsilicon framework metal ions or complexes are of formal charge or valence of $+4$, then the framework is neutral and no ion exchange capacity is developed. Crystallization directing agents commonly known as templating agents such as organic amines or amine cationic species may also be present in the structures after calcination in varying amounts, preferably not exceeding 10 wt. %, more preferably not exceeding 5 wt. %.

The ratio of framework silicon to framework iron in the compositions according to the invention is typically in the range from 2 to about 100,000, preferably 2 to about 15. In the case of cationic frameworks such as iron sodalite, the degree of framework incorporation of iron (III) may be estimated from the sodium exchange capacity. For example, in preparation of iron sodalite, where the Fe/Na atomic ratios after washing out excess sodium species and calcining are about 0.8 plus or minus 0.05, it is estimated that about 20 atomic % of the iron is not in the framework but may exist as occluded or ion exchanged moieties in the calcined zeolites.

Sodalite is a preferred framework structure according to the invention, since it is possible to obtain relatively high loadings of iron in sodalite. Preferred structures are those which contain four rings of tetrahedral atoms (Si, Fe, etc.) since these are expected to favor the formation of iron sites relatively close together but not adjacent. Without limitation to a particular theory, the mechanism of catalysis may involve more than one iron site or an iron plus a silicon site acting in concert, so that greater iron loadings provide proximate iron sites with increased catalytic activity.

The catalysts used according to the invention may be made according to known procedures for making silicoferrate catalysts. (Silicoferrates may be referred to in the prior art as ferrisilicates). The procedure may involve the autoclaving of an aqueous solution of a silicate, an iron salt and a template and water washing, drying and calcining the solid product of the autoclaving. The extent of the calcination is controlled to avoid over-calcination, which may be detrimental to the activity of the catalyst, and under-calcination, which also may be detrimental because of leaving too much template in the structure.

The feedstock for the process of the invention is a hydrocarbon or an oxygenated hydrocarbon having 1 to 10 carbon atoms in the molecule. Hydrocarbon feedstocks include aliphatic, aromatic and cycloaliphatic hydrocarbons, such as methane, ethane, ethylene, propane, n-butane, isobutane, butylenes or mixtures of light alkanes such as natural gas or of alkanes and alkenes in naturally occurring compositions or process streams, hexanes, decanes, benzene, toluene, xylene, naphthalene, cyclohexane, methyl cyclohexane, ethyl cyclohexane, tetrahydronaphthalene, decahydronaphthalene and the like. Oxygenates such as alcohols, aldehydes, ketones, esters and the like are prevalent among the products of oxidation of such hydrocarbons. Products of oxidative coupling are obtained in some instances, for example 2,3-dimethylbutane as oxidative coupling product of propane. Oxygenated hydrocarbon feedstocks include for example methanol, butanols, acetone and higher ketones, aldehydes, valeric acid, phenol, cyclohexanol and the like. The products of oxidation are the further oxygenated derivatives of such feedstock, by further oxidation of functional groups or oxidation at additional points in a carbon chain or both.

In one embodiment the oxidation is carried out in a packed bed tubular reactor at temperatures between 300° and 600° C. and preferably between 350 and 475° C. at pressures between 1 atmosphere and 100 atmospheres and preferably between 10 and 70 atmospheres, with gas hourly space velocities of from 100 to 30,000 and preferably from 500 to 15,000 $hr^{-1}$ using air or oxygen as the oxidizing gas in combination with the light hydrocarbon. When air is used as the oxidant, hydrocarbon/air ratios of between 0.1 to 10 and preferably 0.5 to 5 are effective. When oxygen is used, hydrocarbon/oxygen ratio can be from 0.5 to 50 and preferably 5 to 25. Some of these ratios are within explosive limits and care should be taken to operate behind barricades or similarly shielded devices when running in the explosive region. Water may optionally be fed to the reactor with the hydrocarbon-oxidant mixture or after the reactor to capture oxygenated products which are formed. Other reactor configurations can be used as well which are well known to those skilled in the art.

The catalysts used in the process of the invention are particularly suitable for the oxidation of methane to methanol in the vapor phase, a reaction which, as previously disclosed, has been subject to problems in the prior art, which are overcome by the process of the invention.

The following examples illustrate the invention:

EXAMPLE 1

A silicoferrate, iron sodalite, was synthesized by a modification of the method of Szostak and Thomas supra. A solution of 500 g. sodium silicate solution (Fisher Scientific) and 108 g. sodium hydroxide in 200 g. deionized water was prepared and designated solution A. A second solution, solution B, was prepared by adding 82 g. of 98% sulfuric acid and 80.4 g. of iron (III) nitrate nonahydrate (Aldrich) to 200 g. deionized water with stirring. Solution A and solution B were mixed by alternate addition of small aliquots of each to a beaker fitted with an overhead stirrer. Solution C was prepared by adding 82.7% tetramethylamononium chloride (Aldrich) to 137 g. deionized water.

Solution C was then rapidly added to the mixture of A and B with vigorous stirring. The resulting tan slurry had a relative molar composition ratio of 1.0 $Fe_2O_3$: 24.2 $SiO_2$ 20.7 $Na_2O$: 7.6 TMACl: 465 $H_2O$ and a pH of 11.5 The slurry was stirred without additional cooling for 15 minutes then charged to a Teflon lined 2 liter autoclave, sealed, and purged with argon. The reactor was pressurized to 200 psig with argon and allowed to crystallize with stirring at 168°–172° C. for 68 hours. The reactor product was washed with 1 liter of hot distilled water and 3 liters of room temperature distilled water and dried for 2 days at 125° C. in air. The recovered dried product (80.3 g.) was then calcined in an ebullating bed reactor under argon at 540° C. for one hour and in air at 540° C. for two hours. Chemical analysis indicated 10.6% by weight iron, and BET surface area measurement indicated 2.9 $m^2g^{-1}$. A portion of the calcined product (46 g.) was impregnated with a binder consisting of 17 g. sodium silicate solution (Fisher Scientific) in 75 ml of water, dried at 125° C. overnight, ground and sized to 18/35 mesh, and calcined in a tube furnace exposed to air at 550° C. for one hour.

Chemical analysis indicated that the sample contained 10.11% Fe, 30.23% Si, 0.007% $SO_4^{2-}$, 0.018% Cl, and 4.03% Na, by weight, somewhat higher than the expected percentage of iron after dilution with the binder, which was 9.5%.

Given in Table I is a list of the major peaks obtained in the x-ray diffraction pattern of the above calcined sample prior to addition of binder, using CuK radiation and a solid state detector. The diffraction pattern of hydroxysodalite is given for reference. A small amount of a cancrinite phase may be present in the calcined sample.

TABLE I

| Calcined Sample | | Hydroxysodalite (hydrated, synthetic) | |
|---|---|---|---|
| 2-Theta | Relative Intensity | 2-Theta | Relative Intensity |
| 14.05 | 100 | 34.92 | 100 |
| 24.24 | 84 | 24.54 | 90 |
| 24.46 | 53 | 24.46 | 89 |
| 19.78 | 37 | 24.49 | 88 |
| 34.49 | 17 | 14.08 | 49 |
| 31.47 | 11 | 31.89 | 27 |
| 69.17 | 10 | 43.02 | 23 |
| 11.13 | 10 | 43.08 | 22 |
| 31.79 | 8 | 58.7 | 10 |
| 31.24 | 8 | | |
| 51.88 | 7 | | |
| 11.60 | 7 | | |
| 27.47 | 6 | | |
| 34.65 | 6 | | |
| 20.21 | 5 | | |
| 20.32 | 5 | | |
| 52.39 | 5 | | |
| 40.17 | 5 | | |
| 17.06 | 5 | | |
| 13.42 | 5 | | |
| 61.76 | 4 | | |
| 58.52 | 4 | | |
| 43.12 | 4 | | |

The catalyst thus prepared was used in the vapor-phase oxidation of methane to methanol as follows:

The catalyst was loaded into a glass-lined stainless steel reactor immersed in a sand bath heater and a 3/1 methane/air mixture was passed through the reactor at flow rates from 35 to 800 ml/min at room temperature and atmospheric pressure. 4cc of 18–35 mesh catalyst were used. Water entered the system near the exit port of the reactor at a rate of 15 cc/min. The water captured the methanol in a knock-out vessel and after passage through a back-pressure regulator the gases were passed through a wet test meter into a gas buret which was sampled hourly. The aqueous methanol was analyzed by gas chromatography and the effluent gases were analyzed by both gas chromatography and mass spectrometry. Downstream traps showed that at least 95% of the methanol was captured in the water solution.

Table II shows the results obtained in various runs with the catalyst prepared in this example. After steady state was achieved, a minimum of four replicate measurements taken hourly provided the data given in Table II. In addition to the products shown in Table II, minor amounts of ethane, ethylene, propane and propylene are also formed in some instances. Table III compares the results obtained with the iron sodalite catalyst of this invention with similar runs using reactor packings of glass beads or hydroxysodalite control not containing iron, prepared as follows: Sodium aluminate (Fisher Scientific) (105 g.) plus 34.18 g. solid NaOH were added to 80 g. deionized water and allowed to stand 3 days. After this time, the mixture was warmed (still only partially dissolved) and added to "Nbrand" sodium silicate solution (PQ Corp) (300 g.) with mixing. The pH of the resulting slurry was 12, and its molar composition ratio was $Al_2O_3$: 3.0 $SiO_2$: 2.8 $Na_2O$: 31 $H_2O$. The slurry was charged into a Teflon ® lined 2 liter autoclave, sealed, purged with argon, and pressurized to 200 psig with argon. The sample was allowed to crystallize with stirring at 104°–116° C. for 6 hours. The recovered lump product was washed with 1 liter hot deionized water and 2 liters of room temperature water, dried overnight at 125° C. (136.7 g.), and ground and sieved to 18/35 mesh. The sized product was calcined in two portions at 5° C./min to 540° C. and held for 3 hours in a tray exposed to air. Chemical analysis indicated 7.37% Na, 19.75% Si and 16.29% Al, by weight; BET surface area was 32 m$^2$g$^{-1}$. A powder x-ray diffraction pattern of the product was used to identify the crystalline phase as hydroxysodalite; no other crystalline phase was detected.

Figure 2:
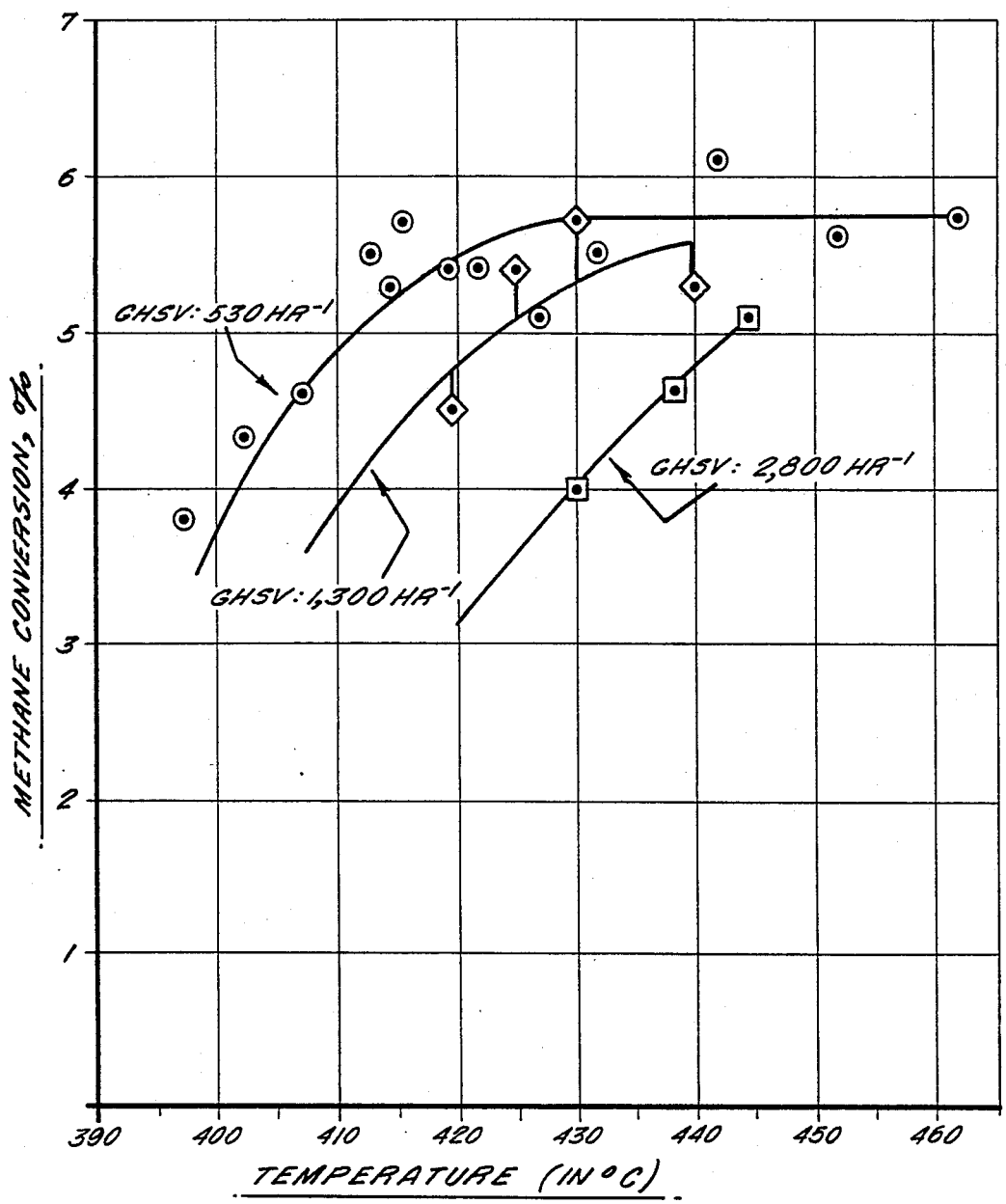

The invention will be further described with reference to the drawings, in which FIG. 1 is a plot of selectivity against reaction temperature at various gas hourly space velocities and FIG. 2 is a plot of methane conversion against temperature at various gas hourly space velocities.

FIG. 1 indicates that at each space velocity used, there is an optimum temperature for maximizing selectivity over iron sodalite.

FIG. 2 indicates the pattern of variation of conversion with temperature over iron sodalite under various conditions.

TABLE II

EFFECT OF SPACE VELOCITY AND TEMPERATURE ON THE [FE] SODALITE CATALYZED OXIDATION OF METHANE

| Run | GHSV hr$^{-1}$ | Temp. °C. | Product mmoles/hr. CH$_3$OH | CO | CO$_2$ | O$_2$ Used mmoles/hr. | CH$_3$OH Sel. % | CH$_4$ Conv. % | O$_2$ Conv. % |
|---|---|---|---|---|---|---|---|---|---|
| 1 | 530 | 397 | 1.64 | 0.73 | 0.43 | 3.1 | 59 | 3.8 | 62 |
| 2 | 530 | 402 | 2.01 | 0.70 | 0.47 | 3.7 | 63 | 4.3 | 74 |
| 3 | 530 | 407 | 2.14 | 0.66 | 0.56 | 3.8 | 64 | 4.6 | 76 |
| 4 | 530 | 413 | 2.72 | 0.75 | 0.63 | 3.9 | 66 | 5.5 | 78 |
| 5 | 530 | 414 | 2.76 | 0.6 | 0.58 | 4.5 | 70 | 5.3 | 90 |
| 6 | 530 | 416 | 2.95 | 0.68 | 0.61 | 4.5 | 70 | 5.7 | 90 |
| 7 | 530 | 418 | 2.73 | 0.71 | 0.59 | 4.5 | 68 | 5.4 | 91 |
| 8 | 530 | 422 | 2.58 | 0.94 | 0.42 | 4.6 | 65 | 5.4 | 92 |
| 9 | 530 | 427 | 2.72 | 0.94 | 0.47 | 4.6 | 66 | 5.1 | 92 |
| 10 | 530 | 432 | 2.57 | 1.02 | 0.44 | 4.5 | 63 | 5.5 | 90 |
| 11 | 530 | 442 | 2.91 | 1.13 | 0.44 | 4.5 | 64 | 6.1 | 90 |
| 12 | 530 | 452 | 2.42 | 1.18 | 0.43 | 4.7 | 59 | 5.6 | 94 |
| 13 | 530 | 462 | 2.47 | 1.27 | 0.46 | 4.7 | 58 | 5.7 | 94 |
| 14 | 1,300 | 419 | 4.81 | 2.24 | 1.17 | 8.2 | 59 | 4.5 | 65 |
| 15 | 1,300 | 425 | 6.34 | 2.24 | 1.44 | 9.6 | 63 | 5.4 | 77 |
| 16 | 1,300 | 430 | 6.48 | 2.52 | 1.51 | 9.8 | 62 | 5.7 | 79 |
| 17 | 1,300 | 440 | 5.82 | 2.42 | 1.63 | 10.0 | 59 | 5.3 | 80 |
| 18 | 2,800 | 430 | 8.14 | 5.30 | 2.13 | 14.9 | 52 | 4.0 | 56 |
| 19 | 2,800 | 438 | 9.76 | 5.55 | 2.48 | 16.6 | 55 | 4.6 | 63 |
| 20 | 2,800 | 444 | 10.32 | 6.00 | 2.78 | 17.3 | 54 | 4.9 | 65 |
| 21 | 5,800 | 437 | 8.22 | 8.56 | 2.27 | 17.5 | 43 | 2.4 | 32 |
| 22 | 5,800 | 449 | 11.24 | 10.21 | 3.27 | 24.0 | 45 | 3.1 | 44 |
| 23 | 5,800 | 451 | 12.81 | 11.37 | 3.76 | 27.4 | 46 | 3.5 | 51 |
| 24 | 5,800 | 455 | 13.13 | 12.25 | 3.89 | 29.1 | 45 | 3.7 | 53 |
| 25 | 5,800 | 459 | 13.28 | 13.18 | 3.77 | 28.2 | 44 | 3.9 | 53 |
| 26 | 11,600 | 453 | 9.62 | 13.07 | 2.74 | 25.3 | 38 | 1.6 | 30 |
| 27 | 11,600 | 466 | 16.28 | 20.65 | 4.13 | 47.5 | 40 | 2.6 | 43 |
| 28a* | 11,600 | 428 | 22.5 | 57.3 | 12.0 | | 24 | 5.7 | |
| 28b* | 11,600 | 434 | 23.6 | 56.9 | 12.0 | | 25 | 5.8 | |
| 28c* | 11,600 | 439 | 19.1 | 57.6 | 12.3 | | 21 | 5.6 | |

*Runs 28a, 28b and 23c were performed first. Runs 1 through 27 followed thereafter. Comparison between the first three and the the last several runs showed that the catalyst had changed while on stream for over 100 hours. CH$_3$OH selectivity = [moles CH$_3$OH/(moles CH$_3$OH + CO + C$_2$S] × 100 CH$_4$ conversion = [moles CH$_3$OH + CO + CO$_2$ + C$_2$'s)/(moles CH$_4$ charged] × 100 O$_2$ conversion = [moles O$_2$ reacted/moles O$_2$ added] × 100

TABLE III

COMPARISON OF METHANE OXIDATIONS OVER FE SODALITE, GLASS BEADS AND HYDROXYSODALITE

| RUN NO. | CATALYST | GHSV HR$^{-1}$ | TEMP. °C. | PRODUCTS MMOLE/HR CH$_3$OH | CO | CO$_2$ | O$_2$ USED MMOLE/HR | CH$_3$OH SEL., % | CH$_4$ CONV, % | O$_2$ CONV, % |
|---|---|---|---|---|---|---|---|---|---|---|
| 3 | Fe Sodalite | 530 | 407 | 2.14 | 0.66 | 0.56 | 3.8 | 64 | 4.6 | 76 |
| 29 | Glass Beads | 530 | 407 | 0.07 | 0.08 | 0.08 | 0.3 | 47 | 0.2 | 7 |
| 30 | Hydroxysodalite | 530 | 404 | — | — | — | — | — | — | — |
| 7 | Fe Sodalite | 530 | 418 | 2.73 | 0.71 | 0.59 | 4.5 | 68 | 5.4 | 91 |
| 31 | Glass Beads | 530 | 418 | 0.50 | 0.33 | 0.20 | 0.8 | 44 | 1.4 | 11 |
| 10 | Fe Sodalite | 530 | 422 | 2.58 | 0.94 | 0.42 | 4.6 | 65 | 5.4 | 92 |
| 32 | Glass Beads | 530 | 422 | 1.00 | 0.57 | 0.20 | 1.3 | 56 | 2.5 | 26 |
| 8 | Fe Sodalite | 530 | 432 | 2.57 | 1.02 | 0.44 | 4.5 | 63 | 5.5 | 90 |
| 33 | Glass Beads | 530 | 430 | 1.75 | 1.07 | 0.31 | 1.9 | 56 | 4.3 | 38 |
| 34 | Hydroxysodalite | 530 | 435 | 0.02 | — | 0.20 | 0.2 | 59 | 0.3 | 4 |
| 11 | Fe Sodalite | 530 | 442 | 2.91 | 1.13 | 0.44 | 4.5 | 64 | 6.1 | 90 |
| 35 | Hydroxysodalite | 530 | 445 | 0.90 | 1.80 | 1.10 | 4.2 | 24 | 5.1 | 84 |
| 28b | Fe Sodalite | 11,600 | 434 | 23.6 | 56.9 | 12.0 | 104 | 25 | 5.8 | 90 |
| 36 | Hydroxysodalite | 11,600 | 434 | 15.8 | 56.7 | 8.4 | 97 | 18 | 5.3 | 90 |

EXAMPLE 37

When methane is oxidized in accordance with example 15, except that the gas feed is a 94/6 methane/oxygen mixture instead of a 3/1 methane/air mixture, and product analysis is done on line so as to capture 100% of the methanol formed, methane is converted to methanol in up to 75% selectivity at up to 7% conversion.

oxide on silica but is slightly inferior with regard to selectivity.

TABLE IV

IRON CATALYSIS FOR METHANE OXIDATIONS

| RUN NO. | CATALYST | GHSV HR$^{-1}$ | TEMP, °C. | PRODUCTS MMOLE/HR | | | O$_2$ USED MMOLE/HR | CH$_3$OH SEL., % | CH$_4$ CONV, % | O$_2$ CONV, % |
|---|---|---|---|---|---|---|---|---|---|---|
| | | | | CH$_3$OH | CO | CO$_2$ | | | | |
| 40 | Fe$_x$O$_y$1SiO$_2$ | 12,000 | 439 | 9.4 | 15.6 | 12.1 | 43.4 | 25 | 2.3 | 37 |
| 41 | [Fe]ZSM-5 | 12,000 | 436 | 14.9 | 53.2 | 10.5 | 89 | 18 | 5.1 | 99 |
| 42 | [Fe]Sodalite | 12,000 | 435 | 23.6 | 56.9 | 12 | 104 | 25 | 5.8 | 94 |
| 43 | Fe$_2$O$_3$/MO$_3$/SiO$_2$/Al$_2$O$_3$ | 2,800 | 450 | 4.8 | 4.5 | 1.0 | 9.6 | 47 | 2.3 | 37 |
| 44 | [Fe]Sodalite | 2,00 | 444 | 10.32 | 6.00 | 2,78 | 17.3 | 54 | 4.9 | 65 |

EXAMPLE 38

When a synthetic hydrocarbon mixture comprising 85% methane, 10% ethane and 5% propane, used as a model for natural gas, was oxidized in accordance with the process of example 7, the selectivity to a mixed $C_1$-$C_3$ liquid oxygenate exceeded 75% and the selectivity to $C_1$, $C_2$ and $C_3$ alcohols exceeded 65%.

EXAMPLE 39

When the synthetic natural gas of the composition given in example 37 is oxidized according to the method of example 36, a liquid oxygenate is formed in 70% selectivity.

A comparison of methane oxidations over iron sodalite, iron ZSM-5, the iron-molybdenum on silica alumina reported in United Kingdom Pat. No. 1,244,001, and iron oxide on silica may be made by an examination of the data in Table IV.

The iron-molybdenum catalyst of Example 43 was prepared as follows:

Dissolved 1.40 grams of ammonium molybdate in 10 ml. of hot deionized water. Weighed out 26.26 grams of silica-alumina 18/35 mesh into a drying dish. Poured the ammonium molybdate solution over the silica-alumina and stirred for 5 minutes. Then dried in 125° C. oven for ½ hour. Calcined in muffle furnace programmed to heat at 5° C./min. to 540° C. and hold for 2 hours. Temperature actually reached 610° C. Removed sample from drying oven. Ground and sieved to 18/35 mesh. Recovered 19.54 gram of 18/35 mesh. Put in drying dish. Dissolved 2.09 grams of ferric nitrate in 10 ml. of hot deionized water. Poured the ferric nitrate solution over the sample and stirred for 5 minutes. Dried in the 125° C. oven for ½ hour. Then calcined in the muffle furnace programmed to heat at 5° C./min. to 540° C. and hold for 2 hours. Removed sample from muffle furnace. Sieved to 18/35 mesh. Recovered 20.81 grams of 18/35 mesh.

The iron oxide catalyst was prepared as follows:

Weighed out 80 grams of silica into a drying dish. Weighed out 144 grams of iron (III) nitrate into a 660 ml. beaker and added enough distilled water to make a 80 ml. solution. Then impregnated the silica with the iron (III) nitrate solution. Dried in the 125° C. oven overnight. Removed from the drying oven and calcined as follows: Heated at 3° C. per minute to 450° C. and held for 5 hours. Weight recovered after calcining 105.34 grams.

Iron sodalite is superior to the above materials. It should also be noted that iron ZSM-5 is superior in methanol production and methane conversion to iron oxide on silica but is slightly inferior with regard to selectivity.

EXAMPLE 45

A mixture of 20% air and 80% propane (total pressure=50 psig) was passed over iron sodalite at a gas hourly space velocity of 370 hr$^1$. Reaction temperature was 360° C. Toluene was injected at the effluent end of the reactor and a toluene solution of reaction products flowed through a cool water condenser into a Jurgeson gauge where the liquid was periodically isopropylalcohol (10.4%),2,3-dimethylbutane (16%), CO (20%), CO$_2$ (11%), acetaldehyde (0.4%), ethane (7%), ethylene (4%), propylene (19%), isoC$_4$'s (7%), methane (11%).

EXAMPLE 46

When ethane is oxidized in accordance with the process of example 7, an oxygenate containing acetaldehyde and ethanol is produced.

The invention claimed is:

1. An oxidation process comprising contacting a feedstock comprising a hydrocarbon or an oxygenated hydrocarbon having 1 to 10 carbon atoms at a temperature of about 350° to 550° C. with air or oxygen and in the presence of a catalytically effective amount of a catalyst containing crystalline silicometallate having iron incorporated in the structural framework.

2. Process according to claim 1 wherein the catalyst contains nonframework iron.

3. Process according to claim 2 wherein the total amount of iron in the catalyst is in the range from 0.1 to 40 weight percent.

4. Process according to claim 2 wherein the amount of framework iron in the catalyst is in the range from 1 to 20 weight percent.

5. Process according to claim 1 wherein said crystalline silicoometallate is a sodalite analog.

6. Process according to claim 1 wherein said crystalline silicometallate is a mordenite analog.

7. Process according to claim 1 wherein said crystalline silicometallate is ZSM-5 analog.

8. Process according to claim 1 wherein the feedstock is methane, the process is carried out in the vapor phase and the methane is converted to methanol.

9. Process according to claim 1 wherein the feedstock is natural gas and the process is carried out in the vapor phase.

10. Process according to claim 1 wherein propane is converted to diisopropyl.

11. Process according to claim 1 wherein the feedstock contains at least one alkane.

12. Process according to claim 1 wherein the feedstock contains at least one alkene.

13. Process according to claim 1 wherein the feedstock contains at least one aromatic hydrocarbon.

* * * * *